US009075038B2

(12) United States Patent
Tumiatti et al.

(10) Patent No.: US 9,075,038 B2
(45) Date of Patent: Jul. 7, 2015

(54) INTEGRATED METHODS FOR CORROSIVITY, AGEING AND FINGERPRINTING DETERMINATION, AS WELL AS DIAGNOSIS, DECONTAMINATION, DEPOLARISATION AND DETOXIFICATION OF OILS

(75) Inventors: Vander Tumiatti, Rosta (IT); Shubhender Kapila, Rolla, MO (US); Carlo Maria Roggero, Turin (IT); Stefano Di Carlo, Turin (IT); Michela Tumiatti, Turin (IT); Riccardo Maina, Turin (IT); Kyle R. Anderson, California, MO (US)

(73) Assignee: SEA MARCONI TECHNOLOGIES DI VANDER TUMIATTI S.A.S., Collegno (Turin) (IT)

( * ) Notice: Subject to any disclaimer, the term of this patent is extended or adjusted under 35 U.S.C. 154(b) by 906 days.

(21) Appl. No.: 13/130,156

(22) PCT Filed: Dec. 16, 2009

(86) PCT No.: PCT/IB2009/055778
§ 371 (c)(1),
(2), (4) Date: May 19, 2011

(87) PCT Pub. No.: WO2010/070590
PCT Pub. Date: Jun. 24, 2010

(65) Prior Publication Data
US 2011/0223672 A1 Sep. 15, 2011

(30) Foreign Application Priority Data
Dec. 16, 2008 (IT) .................. TO2008A0936

(51) Int. Cl.
*G01N 33/26* (2006.01)
*G01N 33/28* (2006.01)

(52) U.S. Cl.
CPC ............. *G01N 33/287* (2013.01); *Y10T 436/18* (2015.01); *G01N 33/2876* (2013.01)

(58) Field of Classification Search
USPC .................... 436/6, 60–61, 119–121
See application file for complete search history.

(56) References Cited

U.S. PATENT DOCUMENTS

| 1,769,463 | A | * | 7/1930 | Rice | 73/86 |
|---|---|---|---|---|---|
| 2,679,752 | A | * | 6/1954 | Metler | 436/6 |
| 3,791,803 | A | * | 2/1974 | Andress et al. | 44/343 |
| 3,882,032 | A | * | 5/1975 | Bird et al. | 508/557 |
| 3,884,932 | A | * | 5/1975 | Andress, Jr. | 548/257 |
| 3,969,237 | A | * | 7/1976 | Andress, Jr. | 508/227 |
| 4,014,894 | A | * | 3/1977 | Andress, Jr. | 548/257 |
| 4,237,733 | A | * | 12/1980 | Kolb et al. | 73/864.21 |
| 4,450,424 | A | * | 5/1984 | Sadler et al. | 336/94 |
| 4,476,733 | A | * | 10/1984 | Chlosta et al. | 73/863.91 |
| 4,808,538 | A | * | 2/1989 | Roffey et al. | 436/6 |
| 5,012,845 | A | * | 5/1991 | Averette | 141/329 |
| 5,157,963 | A | * | 10/1992 | Muyskens et al. | 73/53.05 |
| 5,332,900 | A | * | 7/1994 | Witzke et al. | 250/341.1 |
| 5,516,969 | A | * | 5/1996 | Krasznai et al. | 588/20 |
| 5,874,309 | A | * | 2/1999 | Chang et al. | 436/6 |
| 6,074,610 | A | * | 6/2000 | Huang et al. | 422/550 |
| 6,096,695 | A | * | 8/2000 | Lam et al. | 508/570 |
| 6,132,686 | A | * | 10/2000 | Gallup et al. | 422/130 |
| 6,146,895 | A | * | 11/2000 | Green et al. | 436/47 |
| 6,294,387 | B1 | * | 9/2001 | Yepez et al. | 436/6 |
| 6,365,413 | B1 | * | 4/2002 | Hall et al. | 436/60 |
| 6,756,346 | B1 | * | 6/2004 | Baba et al. | 508/433 |
| 7,025,138 | B2 | * | 4/2006 | Kurkjian et al. | 166/250.05 |
| 7,553,449 | B2 | * | 6/2009 | Yeganeh et al. | 422/53 |
| 8,241,916 | B2 | * | 8/2012 | Toyama et al. | 436/120 |
| 2003/0027346 | A1 | * | 2/2003 | Onwumere et al. | 436/60 |
| 2004/0147410 | A1 | * | 7/2004 | Milner et al. | 508/195 |
| 2004/0241875 | A1 | * | 12/2004 | Dales et al. | 436/180 |
| 2005/0095717 | A1 | * | 5/2005 | Wollenberg et al. | 436/60 |
| 2005/0181512 | A1 | * | 8/2005 | Wollenberg | 436/60 |
| 2006/0063263 | A1 | * | 3/2006 | Yeganeh et al. | 436/6 |

FOREIGN PATENT DOCUMENTS

GB 2200469 * 8/1988
JP 59-095463 A 6/1984

OTHER PUBLICATIONS

Levin, H. et al, Industrial and Engineering Chemistry 1942, 14, 107-109.*
Tumiatti, V. et al, IEEE International Symposium on Electrical Insulation 2006, 400-402.*
Ott, L. S. et al, Journal of Sulfur Chemistry 2007, 28, 493-504.*
ASTM International Designation D1662-08 "Standard Test Method for Active Sulfur in Cutting Oils" 2008, 3 pages.*
Tumiatti, V., My Transfo 2008—Victor Sokolov Lecture 8 pages, http://www.seamarconi.com/downsm/myt2008/paperTUMIATTI_Sokolov%20lecture3.pdf.*
Tumiatti, V., My Transfo 2008—Victor Sokolov Lecture Slides 21 pages, http://www.seamarconi.com/downsm/myt2008/pptMyT08_lecture_SOKOLOV-Tumiatti.pdf.*
Garner, F. H. et al, Journal of the Institute of Petroleum 1931, 17, 451-463.*

(Continued)

*Primary Examiner* — Arlen Soderquist
(74) *Attorney, Agent, or Firm* — Sughrue Mion, PLLC

(57) ABSTRACT

The methods of the invention are aimed toward the determination of corrosivity, ageing, fingerprinting and contaminants, as well as the functional diagnosis, decontamination, depolarization and detoxification of oils and technical fluids, such as mineral insulating, natural and/or synthetic esters, lubricants, hydraulic fluids, diathermic fluids and technical fluids in general, used in apparatuses and equipment, such as electric transformers, reactors, bushings, switches and turbines, for the generation, transmission, distribution and use of power.

10 Claims, 5 Drawing Sheets

(56) References Cited

Figure 1:
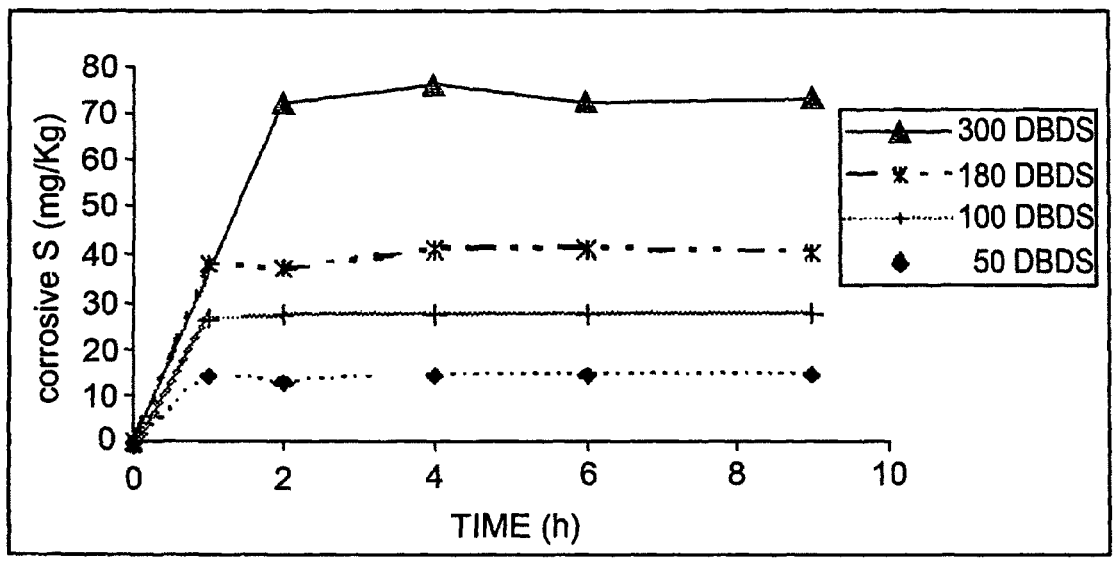

OTHER PUBLICATIONS von Fuchs, G. H. et al, Industrial and Engineering Chemistry, Analytical Edition 1941, 13, 306-312.*
Loane, C. M. et al, Industrial and Engineering Chemistry, Analytical Edition 1945, 17, 89-95.*
Garcia-Perez, M. et al, Energy & Fuels 2006, 20, 786-795.*
Prevost, T. A, "Reviw of Test Methods to Detct Corrosive Sulfur in Insulating Oil" Weidmann-ACTI Inc. Sixth Annual Technical Conference, St. Petersburg, FL Nov. 12-14, 2007.*
Staeger, H. C., Industrial and Engineering Chemistry 1925, 17, 1272-1275.*
MacCoull, N. et al, SAE Journal 1942, 50, 338-345.*
Wasson, J. I. et al, Industrial and Engineering Chemistry 1953, 45, 197-200.*
ASTM D1934-95 1995, 3 pages.*
Caokai, T. et al, Petrochemical Corrosion and Protection 2000, 17, 39-42. (in Chinese with English language abstract).*
Hau, J. L. et al, Revista de Metalurgia Madrid Volume Extra 2003, 116-123.*
Sobolev E P, et al., "Evaluation of Motor Oil Corrosivity at High Temperatures," Chemistry and Technology of Fuels and Oils, Sep. 1982, pp. 523-525, vol. 18, No. 9-10.
F. Scatiggio, et al., "Corrosive Sulfur in Insulating Oils: Its Detection and Correlated Power Apparatus Failures," Jan. 2008, pp. 508-509, vol. 23, No. 1.
J.R. Nanda, et al., Sulfur Contamination in Insulating Oils—The Copper Strip Corrosion Test, Journal of the Institution of Engineers, India, Aug. 1970, pp. 285-589, vol. 50, No. 12.
"Standard Test Method of Corrosive Sulfur in Electrical Insulating Oils[1]," D 1275-06, Annual Book of ASTM Standards, Jan. 1, 2006, pp. 107-110, vol. 10.03.

\* cited by examiner

INTEGRATED METHODS FOR CORROSIVITY, AGEING AND FINGERPRINTING DETERMINATION, AS WELL AS DIAGNOSIS, DECONTAMINATION, DEPOLARISATION AND DETOXIFICATION OF OILS

CROSS REFERENCE TO RELATED APPLICATIONS

This application is a National Stage of International Application No. PCT/IB2009/055778 filed Dec. 16, 2009, claiming priority based on Italian Patent Application No. TO2008A000936 filed Dec. 16, 2008, the contents of all of which are incorporated herein by reference in their entirety.

FIELD OF APPLICATION

The invention describes the integrated methods for the determination of the corrosivity, the aging, the "fingerprint" as well as the functional diagnosis, decontamination, depolarisation and detoxification of oils (e.g. mineral insulating; natural and/or synthetic esters; lubricants; hydraulic fluids; diathermic fluids; technical fluids in general) which provide a vital function for the correct operation of strategic equipment and fleets of equipment (e.g. electric transformers, reactors, bushings, switches, turbines etc.) for the generation, transmission, distribution and use of power (electric, thermal, mechanical etc.).

STATE OF THE ART

Operational Scenario

The oils described in the previous chapter ("field of application") must satisfy the law requirements, technical standards and supply specifications for the specific applications required by the fleet of equipment.

Technical oils have vital functions for the equipment itself and in this field, a management methodology is metaphorically used similar to "human blood, being in contact with internal organs, for which diagnostic tests and dialysis therapies are applied". The composition and formulation of the oils is very complex for the nature of the bases used, the type of refining of the various fractions (naphthenic, paraffinic, aromatic etc.), for the physical-chemical and toxicological characteristics of the various substances present in the matrix (up to over 3,000) and for the interactions of the additive packages with the internal components of the equipment (copper, solid insulations etc.). During their life cycle, oils are exposed to normal aging, thermal stresses (generalised thermal oxidation, hot spots<150° C., 150-300° C., 300-700° C., >700° C.), electric stresses (generalised corona effect, partial discharges, power arches etc.) that can reduce the operational life of the equipment and/or its components (e.g. solid insulations, Kraft paper etc.) and induce critical incidences.

Under some circumstances, an abnormal aging and/or accelerated corrosion processes can cause failures to the equipment itself with:

a—direct damages to people and assets with the loss of economical and functional value (e.g. explosion and/or fire, reduction of the operational life, disposal as waste);
b—indirect damages for loss of production and penalties (e.g. power blackouts, interruption of a public service under governmental concessions etc.);
c—environmental damages for the actions of decontamination, disposal of wastes and remediation (matrices: air, water, soil, food, areas/surfaces, systems, equipment etc.) caused by spills and/or emissions of dangerous and persistent substances which can induce unreasonable risks for workers, public health and the environment.

Some contaminants are not naturally present in the oils nor are formed during the use, but are additives, i.e. chemical substances added to the oils to improve some properties (IEC-EN 60296 art. 3.3). Besides the normal requisites prescribed for the oils, it is necessary to provide effective and timely responses to the current and priority operational needs of the sector.

2.1 The First Operational Requirement are the Methods of Quantitative Determination of the "Total Corrosive Sulphur" in New Oils (for New Equipment or the Topping-Up of Equipment in Operation) and for the Periodic Inventory of the Oils in Operation on Fleets of Equipment.

In a power transformer, for example, the insulating oil represents about 25% of the weight of the equipment and about 5-7% of its financial value. In the OECD area (8 Countries) just for the sector relative to the generation of electric power (excluding transmission and distribution for industrial use) the mass of oil is estimated at 10 billion kg (year 1990) at an average current replacement cost of 1.5-2 Euro/kg, packaged in 200 Lt drums.

In 2005, Sea Marconi initially identified DBDS (DiBenzylDiSulphide) in a naphtenic base, non-inhibited oil, produced by a market leader, with a typical "anamnesis" and "signs" characterised by a high correlation between the type of oil with a low concentration of total sulphur (<500 mg/kg) and a high ratio of infancy failures on transformers and reactors (in Italy, Brazil, and Columbia). The DBDS resulted being a corrosive sulphur contaminant used as additive in the oils for its specific anti-oxidant properties. In 2006, DBDS has been found in the main new insulating oils (rate of positive up to 100% on naphtenic uninhibited oils in Europe, North and South America) and also confirmed on a representative rate of the population of transformers and reactors built after 1990-1992 (rate of positive up to 60-70% on some fleets of equipment). As a response to such a scenario, a "DBDS & Corrosion Free" program was developed, with a methodological approach equivalent to the one used for the environmental protection relative to "POPs & PCBs Free". The actions and countermeasures have a high priority for their global relevant impact (potential damages estimated in several billion Euros). The global impact of this technological risk is a priority also under an insurance profile, since the DBDS and Corrosive Sulphur risk" cannot be classified as an "Accidental of Product defect" or as "Cause of Force Majeure" in insurance coverage for equipment failures. As an example, a single case of failure in southern Italy on a "Step-up" generation transformer built in 1998 (192MVA at 400 KV) the direct and indirect damages were estimated at several tens million Euro (only partially compensated by insurance coverage). The use of DBDS in mineral oils started, most probably, in 1988 with the introduction of a new hydrogenation process of oils with naphtenic base, which eliminates also the main sulphur components, including natural anti-oxidants. This sulphur compound is very corrosive toward copper and must not be present in new insulating oils ("sulphur compound, very corrosive to metal surfaces—i.e. steel, copper and silver—switchgear contacts—and shall not be present in new oil"—IEC—EN 60296 art. 6.10).

Mineral oils contaminated by DBDS made a significant percentage of the worldwide production of insulating oils, estimated at more than one million tons per year, and have been used in millions of equipment in several Countries, for a value of billions Euro. The normal maintenance procedures of the oils in operation in equipment (e.g. topping-up, change, reconditioning and regeneration treatments of the oil etc.) can spread the "corrosive sulphur" risk to entire fleets of equipment through DBDS cross-contamination, similar to PCBs. It has been experimentally demonstrated that DBDS in the oil can trigger a corrosive action, under normal operational conditions of the equipment, at relatively low concentrations (10-15 mg/kg).

Operational experiences on contaminants such as PCBs and DBDS show the criticality of topping-ups with contaminated oils. Risk factors are emphasised for topping-ups by contaminated oil (5-10% of the oil charge) or for the change of a single oil charge to obtain (after 90 days equilibrium) with a critical concentration (10-15% of the initial concentration of the charge) under the effect of the progressive release of contaminants of impregnation oil of the active part of solid insulation (10-15% in weight; a typical case is the factory test of power transformers).

Such corrosive contaminant has been determined in the oil contained by equipment in operation in the typical range 150-250 up to 500 mg/Kg. (Maim R., Scatiggio F., Kapila S., Tumiatti V., Tumiatti M. and Pompili M. "Dibenzyl disulphide (DBDS) as corrosive sulphur contaminant in used and unused mineral insulating oils" published on CIGRE SC2 web site, 2006 http.//www.cigre-a2.org/>Publications>Other documents).

The reaction of DBDS and other sulphur based corrosive compounds with copper create, under normal operation conditions, creates the formation of copper sulphide ($Cu_2S$) ("under the normal operating conditions of the transformer"— CIGRE WG A2-32 Copper sulphide in transformer insulation, Final Report, Draft 8 Nov. 2008).

The conversion of DBDS into copper sulphide starts at about 100° C. and brings to the formation and release of conductive particles, which, depositing on the insulating paper, degrade the insulating properties, causing electric discharges and equipment failures (V. Tumiatti, R. Maim, F. Scatiggio, M. Pompili and R. Bartnikas, "Corrosive sulphur in mineral oils: its detection and correlated transformer failures" Proc IEEE Int. Symposium on Electrical Insulation, Toronto, June 2006).

In spite of the numerous failures and the potential impact of sulphur corrosive components on the reliability and availability of the fleets of equipment, the methods currently available for their determination in the oils are only of an empirical and qualitative character, with considerable uncertainty of measure, inducing into ineffective and/or wrong decisions and actions. These methods are based upon a visual observation and the perception of the colour change of the surface of copper and/or the paper wrapping it after interaction with the oil (method ASTM 1275B 2006: 250 ml of oil, 300 $mm^2$ copper strip 150° C., 48 h, without air/oxygen; Method CCD test, Copper Deposition Test, IEC-EN 62535 2008-10 "Method for the determination of potentially corrosive sulphur in new and used oils", 15 ml of oil, 570 $mm^2$ copper strip covered by Kraft paper, 150° C., 72 h with air).

Current methods can provide contradictory results. It has been demonstrated that the CCD test can produce "False Positive" results (up to 80% of "Potentially Corrosive"), in case of used oils with used and/or degraded oils and "False Negative" (up to 100% of "Non Potentially Corrosive"), in case of oils with DBDS, but with passivating additives masking the visual effects during the 72 hour test (R. Maina, V. Tumiatti, "CCD applied to aged oils", presented at the CIGRE WG A2-32, October 2007).

The CCD test includes, in case of doubt in the interpretation of the results of the inspection of the paper, the composition of the precipitate must be analysed using other methods, such as, for example, SEM-EDX ("In case of there are any doubts in the interpretation of the results of inspection of paper, the composition of precipitate should be analysed by other methods—for example by SEM-EDX"—IEC-EN 62535 2008-10 art 6.4). It is well known that SEM-EDX is a complex, very expensive instrumentation, not easily available, providing, in any case, qualitative results only.

To mitigate the corrosive sulphur problem, different techniques have been developed. A first contingent response has been to additive the oil with some metal passivators, in particular derivatives of Benzotriazole (BTA) such as Ciba Irgamet39® and Ciba Irgamet30® in concentrations around 100 mg/kg (ABB patents, J. Hajek, M. O. Dahlund, L. Petterson "Methods and apparatuses for Detecting/reducing harmful substances in oils" U.S. Application No. 60/566,606 Apr. 30, 2004).

Passivators, added to the oil, should theoretically form a protective film on the metal surface preventing the attack by corrosive compounds such as DBDS. It has been experimentally demonstrated that such film cannot be uniform, since it is not capable of providing a robust protection during the life cycle expected from transformers and reactors (about 168, 000 hours at nominal load, equivalent to 25-40 years). It has been reported that several reactors of the same family failed after a few months (12-24 months) after passivation (CIGRE WG A2-32 Copper sulphide in transformer insulation, Final Report, Draft 8 Nov. 2008).

Also, the use of BTA and its derivatives can determine unreasonable risks for workers, public health and the environment due to the mutagenic nature and the correlated risks "Suspected carcinogenic" (National Cancer Institute Technical Report Series No. 881978—US department of Health, Education and Welfare, Public Health Service National Institute of Health). Another critical factor is the functional ineffectiveness of the additive since, in any case, it degrades under normal operational conditions.

The methods described here below for the quantitative determination of "total corrosive sulphur" solve all types of analytical uncertainty and interpretative doubts with results referred to the addition of the corrosive sulphur compounds, including DBDS, with the presence or not of additives (passivating and not) in the oils subject to a test with the above mentioned protocol.

2.2 The Second Operational Requirement are the Methods for the Quantitative Determination of the "Aging & Non-Sulphur Corrosion" of New Oils (for New Equipment or for the Topping-Up of those in Operation) and for the Inventory and/or Periodic Monitoring of Oils in Operation on Fleets of Equipment.

The current oxidation stability of insulating oils is determined by methods ASTM D 2440 or IEC EN 61125. According to these norms, the oil is subject to oxidative conditions, in presence of copper wire, at a typical temperature of 120° C. for a time from 164 up to 500 hours (in case of anti-oxidant inhibitors). However, such methods provide only data of volatile acidity and the formation of sludge, results that do not provide the evaluation and quantification of the critical aging factors, the stability of the oil and its additives and the corrosive action (different from corrosive sulphur) toward copper. Operational experiences, on thousands of transformers, demonstrate a progressive increment (up to over 250 mg/kg for some types of oil and equipment) of dissolved and/or suspended copper (not correlated to DBDS, total sulphur and to "corrosive sulphur"), symptomatic of different corrosion mechanisms (V. Tumiatti-Sea Marconi, E. Serena CIGRE TF 15.01.05-"Stastistical evaluation" Turin November 1997; V. Tumiatti-Sea Marconi CIGRE 2000 Paris).

The methods described here below for the determination of "Aging & Non-sulphur corrosion" are based upon the univocal comparison of acidity, sludge, concentrations and the velocity of formation of water, dissolved gases, (DGA with headspace: CO etc.) of oxidised components (ketones, aldehydes, acids) of the dissolved and/or suspended copper in the oil subject to test with the above mentioned protocol.

2.3. The Third Operational Requirement are the Methods for the Qualitative and Quantitative Determination of Univocal Imprinting of the Formulations "Oil Fingerprint" of New Oils (for New Equipment or the Topping-Up of those in Operation) and for the Inventory and/or Periodic Monitoring of Oils in Operation on Fleets of Equipment.

The current methods for the identification and classification of oils are unspecific, since they are mainly based on the generic characterisation of functional properties (viscosity, density, pour point, flash point etc.) in accordance with, for example, standard IEC EN 60296 2003-11.

The methods described here below for the determination of the "Oil Fingerprint" solve all types of analytical uncertainty and interpretative doubts with results referred to a univocal comparison (qualitative and quantitative) of the profiles of the "ether atoms" present in the formulation of the oils, such as sulphur (S) Oxygen (O), Nitrogen (N) the profile of Carbon (C) with correlated distillation curves of the oils subject to test with the above mentioned protocol.

2.4. The Fourth Operational Requirement are the Methods for the "Functional Diagnosis" of the Oils in Operation in New Equipment ("Zero Point", the Reference Prior to Beginning of Operations) or for the Inventory and/or Periodic Monitoring of the Functional Conditions of the Oils in Operation on Fleets of Equipment.

Current methods are indefinite, since they are based upon a generic characterisation of some functional properties (Colour and aspect, Moisture, Acidity-TAN, Viscosity, Flash Point, Density, Particles etc.) in accordance with, for example, standard IEC EN 60422 2005-10.

The methods described here below for the formulation of a "Functional diagnosis" solve all types of doubts for the precise identification and interpretation of the main "Markers" of the "Diagnostic picture" and for the inventory and/or periodic monitoring of the conditions of the oils in operation in fleets of equipment subject to diagnosis with the above mentioned protocol.

2.5 The Fifth Operational Requirement are the Methods "Integrate Treatment of Oils—Decontamination, Depolarisation and Detoxification" on New Fluids for New Equipment (Zero Point" of Reference Prior to Starting Operation) and for the Periodic Treatment of the Oils in Operation on Fleets of Equipment.

The current methods are unspecific and/or limited to the inspection and treatment of the oils, since they are generic treatments of a physical type—"Reconditioning", elimination under vacuum of moisture, particles and dissolved and adsorption gases—"Reclaiming", with Fuller earths, which are not suitable for the effective elimination critical contaminants (such as corrosive sulphur compounds such as DBDS, POPs-PCBs, ketones, aldehydes, etc) in compliance with, for example, standard IEC EN 60422 2005-10. Such operational practices, in many instances, create the conditions for the propagation of the criticalities to the entire fleet of equipment, caused by "Cross-contamination". The typical decisional scenario is often characterised by confusions and uncertainties bringing to the implementation of ineffective treatments or to an unmotivated change of the oils in operation. The consequences of such actions are elevated management financial and environmental costs, both in terms of disposal of dangerous wastes and in terms of emissions of equivalent $CO_2$. It is well known, in fact, that oil is not a renewable resource and that through the LCA (Life Cycle Analysis) it is determined that for each ton of spent oil disposed of by incineration, five tons of $CO_2$ are produced (Ministry of the Environment and Protection of the Territory and the Seas—Italy D. M. 29 Jan. 2007 Off. Gaz. n. 133 of Jul. 6, 2007 "Issue of the Guidelines for the identification and use of the Best Available Techniques (BAT) on the subject of management of wastes, page 52).

The methods described here below for the "Integrated Treatment of Oils—Decontamination, Depolarisation and Detoxification" solve all types of uncertainty through "Treatment Tests" for the technical and financial feasibility and to improve the most effective formulation of the reagents to be used in targeted treatments. These treatments are performed by stationary or mobile (DMU) system in a discontinuous or continuous mode, in closed-loop also under load. These treatment methods implement the BAT guidelines relative to the best protection of assets under a functional and environmental profile, for the conservation of resources and self-sufficiency.

As a conclusion, the requirements of the sector and the five critical factors pointed-out here above are points of global tension offering the opportunity for the development and use of new management integrated methods, described in this invention.

These methods are capable of providing an effective response with quantitative tests, relative to the main properties and critical correlated factors of the oils, reducing the times and solving the limitations and uncertainties of the current methods (classified as empirical, qualitative and/or unspecific). These methods apply also for the formulation of reagents, simulation tests, quality and traceabilty control, for the optimisation of targeted treatments for the decontamination, selective depolarisation and detoxification of oils containing:

a—corrosive compounds (which include derivatives containing sulphur, such as DBDS—Di Benzil Di Sulphate and other ether-organic compounds);
b—potentially dangerous compounds (such as benzotriazole—BTA—and its derivatives);
c—persistent organic pollutants (POPs such as PCBS etc.);
d—contaminants and polar by-products already present in the formulation and/or generated by the degradation and/or oxidation of the oils (ketones, aldehydes etc.) in the equipment in operation.

These methods satisfy the requisites of the "Best Available Technique—MTD/BAT" in compliance with European Directive 96/61/EC, for the Oil Life Cycle Management—(OLCM), according to technical standards (IEC—EN 60296 2003-11 "Unused mineral insulating oils for transformer and switchgear", and IEC-EN 60422 2005-10 "Mineral insulating oils in electrical equipment—Supervision and maintenance guidance"; etc.) and/or to provide the specific prevention and/or mitigation of damages protection for fleets of equipment in operation ("Life Asset Management—LAM").

DESCRIPTION OF THE INVENTION

This invention consists of integrated methods capable of drastically reducing the reaction tests for corrosivity, typically from 72 to 12 hours, on passivated oils and from 500 to less than 24 hours for the aging tests on inhibited oils, as well as reducing the volumes of oil used (typically from 250 ml to 15-30 ml for the copper strip test) with a fast quantitative evaluation of the properties of the oil being examined and the equipment the oil is in contact with, as, for example, the insulating paper of transformers. The methods include also tests suitable to determine and develop optimised formulations for the decontamination, depolarisation and detoxification treatments of oils.

The invention is based upon five different passages and/or operational options:

I—Accelerated corrosivity test of the oil at 150° C. for 12 hours, in the presence of copper, in vials prepared in controlled atmosphere by a "revolving table" and dedicated "heating and stirring" apparatus.

II—Accelerated aging of the oil at 120° C. for 24 hours, in the presence of copper, in vials prepared in controlled atmosphere by a "revolving table" and dedicated "heating and stirring" apparatus.

III—Fingerprinting and characterization of the oils, before and after the tests, determination of chemical composition and the presence of specific additives (DBDS, copper passivators, DBPC, etc) and/or contaminants.

IV—Diagnosis based upon the interpretation of the results obtained by the tests of Phases I-II-III capable of predicting the effects of the degradation inside the equipment containing the oil in operation.

V—Decontamination, selective depolarisation of corrosive and oxidized compounds and other by-products that have a negative impact on the properties of the fluid that could endanger the equipment, and detoxification of dangerous compounds such as passivator additives and/or POPs, PCBs. The treatment uses a dedicated reagent, liquid and/or solid, formulated with a mixture of chemical compounds (e.g. poly glycols plus a mixture of bases) and catalysers such as non-alkaline metals.

The invention involves the use of specific materials, apparatuses and reagents capable of performing the required tests and treatments. In the corrosivity tests, the copper is in contact with the oil at specific temperatures under shaking conditions; then, through oxidation or reduction, the conversion of the copper sulphide which is formed (insoluble) is done into soluble and easily identifiable species: as an example the sulphides can be oxidised into sulphates, quantifiable by HPLC, ion chromatography or turbidity.

Also, the invention includes the development of an accelerated aging method of the oil, under specific conditions; this method requires the use of part of the same equipment used for the quantification of corrosive sulphur. The oil being examined is exposed to an oxidative atmosphere. The species which are formed during the treatment can be determined and quantified (GC, GC-MS, AED, ICP, etc.). Also, the TAN, the formation of residues (sludge), oxidised molecules (titration, gravimetric methods and FT-IR spectroscopy) and dissolved or suspended copper in the oil for the corrosion not correlatable to sulphur.

The invention also includes tests and the specific formulation of reagents, relative to treatments targeted toward the elimination and/or decomposition of corrosive, oxidised compounds, of contaminants and/or by-products deriving from the functional degradation and aging of the oils, as well as dangerous compounds as BTA additives and POPs-PCBs.

DETAILED DESCRIPTION OF THE INVENTION

The aim of this invention is to provide an integrated method applicable to the different oils described in the filed of application (please refer to point 1).

4.1 Description of the Apparatuses

The apparatuses and the materials used by the methods are described here below:

A—Borosilicate glass vials size from 10 to 100 ml, sealed with special caps (PTFE and butyl rubber) able to perform a preparation of the samples, resisting to test conditions and guaranteeing the sealing for analyses of liquid, solid and gases species generated during the processes.

B—"Revolving table" apparatus used for preparation of samples that can contain from 1 to 100 housings for vials (typically 20). Each vial is saturated by a gas, crimped with a specific instrument under controlled atmosphere conditions (i.e. Argon or Oxygen) under or over pressured with respect to the ambient and filled with oil through a syringe piercing a sealing membrane. According to the test application, each vial can contain specific materials and reagents such as copper powder and a magnetic stirrer for accelerated ageing test, corrosivity and treatment tests.

C—Time-controlled heating and stirring apparatus able to stir (from 0 to 1500 rpm) and to maintain temperature of vials samples with extreme precision, from 0° C. to 350° C. (typically 120-150° C.). The caps of the vials are located out of the steel housings to reduce thermal stress in the sealing zone. When desired, the apparatus can operate uninterrupted for long hours exceeding 1,000 hours (typically from 1 to 24 hours).

4.2 Determination of "Corrosive Sulphur"

A fundamental part of the methods consists in the quantification of corrosive compounds and by-products deriving from their thermal degradation or the reaction with some metals such as copper. The majority of the more frequent corrosive compounds containing sulphur. The DBDS has been chosen as model molecule. It has been found that DBDS readily reacts with copper at temperatures above 100° C.; generating cuprous sulphide, cupric sulphide and a series of products, among them Dibenzilsulphide, toluene, benzilmercaptane, stilbenes and bibenzyl (BB).

The analyses (HRGC-MS and HRGC-AED) of the products obtained by the reaction of the DBDS with copper powder in dodecane at 150° C. under magnetic stirring have demonstrated that the main sub-product is BB. This compound is not normally contained by dielectric fluids, thus it can be used as a "marker" for the quantification of corrosion of the copper caused by the DBDS inside a transformer (see 4.2.1).

The finding and quantification of volatile or semi-volatile organic corrosive compounds can be done through gas chromatographic techniques, whereas the quantification of inorganic salts, such as copper sulphide, can be easily performed according to the method described here below (4.4.2).

4.2.1. Quantification

Corrosive compounds react with metals generating salts and organic by-products. Surprisingly, it is possible to evaluate directly the effects on copper of all the corrosive compounds containing sulphur (not only DBDS) through a quantitative determination of the copper salts. Through a gas chromatography, it is possible to perform a quantitative determination of sub products-markers to evaluate the entity of the corrosion of the metal parts of the transformer. Considering DBDS, we can compare its concentration with the concentration of one of its by-products, bibenzyl (BB), to calculate the quantity of organic sulphur converted into inorganic salts. Lab experiments have shown that DBDS, dissolved in a hydrocarbon matrix in concentration of 300 mg/Kg, and maintained in contact with copper for several hours at 150° C.

is totally converted into the species indicated in FIG. 1. It has been discovered that BB accounts for at least 80% in weight of the total organic by-product fraction. The stoichiometry of the reaction can be expressed as given in eq. 1.

$$DBDS \rightarrow BB + 2Cu_2S \qquad \text{eq. 1}$$

Thus one mole of DBDS will lead to one mole of bibenzyl and two moles of cuprous sulphide.

If one assumes that DBDS conversion to BB is 80%, then the expression takes the form given in eq. 2:

$$gS_{in} = (m_{BB}/0.8) \times 32.07 \times 2 \qquad \text{eq. 2}$$

where
- $gS_{in}$ are the grams of inorganic sulphur formed (corrosive sulphur)
- $m_{BB}$ is mole of bibenzyl BB.
- 0.8 is the correction factor for the incomplete conversion of DBDS into BB.
- 32.07 is the average atomic weight of sulphur.
- 2 is the stoichiometric coefficient of the reaction from DBDS to sulphur.

This formula pertains to DBDS in dielectric oils, but can be extended to other corrosive compounds in other technical fluids, after the necessary amendment (different compounds and consequently different molecular weights and coefficients).

4.2.2 Corrosive Compounds Conversion and Quantification of Copper Salts Resulting from Corrosion.

4.2.2.1 First Stage—Oil/Copper Interaction

The first stage is the reaction of a weighed quantity (5-50 g) of liquid (e.g. insulating oil), with a weighed amount (0.5 to 10 g) of pickled copper powder or granules (1 μm to 5 mm) at temperature above 100° C. (100-200, typically 150° C.) in a gastight throw away borosilicate glass vial (volume 5 to 100 ml) sealed in the revolving table with appropriate pressure resistant PTFE/butyl rubber cap. This reaction occurs under magnetic stirring for the period of time 0.5 to 600 hours, typically 2-12 hours). Here is the sequence of sample preparation:

1) The vial is loaded with the weighed amount of pickled copper and a magnetic bar.
2) The oil is added into the vial while operating in an oxygen-free environment (Argon or Nitrogen) using the "revolving table" apparatus (see clause 4.1).
3) The vial is sealed with caps described in clause 4.1.

Once the sample is ready the thermal treatment begins. To perform it, a precision heating and magnetic stirring apparatus (see clause 4.1) that can process several vials simultaneously has been developed. At the end of the reaction, the second stage starts.

4.2.2.1 Second Stage—Copper Processing

The copper is decanted away from the oil on which additional analyses can be performed later. Copper is rinsed several times with a hydrocarbon solvent such as pentane, n-hexane, heptanes or isooctane. The liquid is then removed and the powder is rinsed under a gentle stream of gas (air, nitrogen, argon) and/or under mild heating (30-60° C.).

The copper is then subjected to different treatments with a common purpose of converting the water-insoluble copper sulphide into soluble species such as cupric sulphate or hydrogen sulphide.

These treatments involve the use of the following materials and reagents:

a) $O_2$+MOH+heat, where M is an alkaline metal, such as sodium or potassium.
b) $NH_4OH/H_2O_2$ (Ammonical Hydrogen Peroxide).
c) Aqua regia
d) $MBH_4$, where M is an alkaline metal. .

Reagents from a) to c) have oxidizing properties and transform copper sulphide into cupric sulphate. Reagent d) is a reducing agent and turns copper sulphide into hydrogen sulphide.

In method a) the vial containing the rinsed and dried copper is added with a weighed amount of an alkaline hydroxide (from 0.01 to 1 g); the vial is sealed and heated to temperatures ranging from 250°-500° C. with a flame or resistive heating element. During this heating stage pure oxygen is made to flow through the vial with two needles—one serves as the inlet while the other serves as the outlet. The oxidation is carried out for several minutes (from 5 to 60). After allowing for cooling the samples to ambient temperature a few grams of water (5-10) are added to the vial. The solution is boiled for a few minutes (5-10) under a gentle oxygen stream. The resulting copper sulphate suspension is then filtered and analysed.

Transformation of copper sulphide into copper sulphate is depicted in eq. 3-5.

$$2Cu_2S + 9/2 O_2 \rightarrow CuSO_4 + SO_2 + 3CuO \qquad \text{eq. 3}$$

$$SO_2 + 2NaOH \rightarrow Na_2SO_3 + H_2O \qquad \text{eq. 4}$$

$$Na_2SO_3 + \tfrac{1}{2}O_2 \rightarrow Na_2SO_4 \qquad \text{eq. 5}$$

In method b) the vial containing the rinsed and dried copper is added with some ml (1-10) of ammonia solution (25-30%) and left under magnetic stirring for copper sulphide solubilisation (1-4 hours). The resultant solution is transferred in a separate flask, reduced to small volume (1-5 ml) under gentle heating and then oxidised with hydrogen peroxide (25-30%). The extraction-reaction process can be repeated several times (2-3), in order to get a complete conversion of sulphide into sulphate. After the oxidation is complete the residual hydrogen peroxide is evaporated away, making the solution ready for analysis.

In method c) in the vial containing the rinsed and dried copper some ml of aqua regia (5-10) are added. Due to the oxidative and complexing properties of aqua regia, copper is turned into cupric nitrate and the sulphide into sulphate. The solution is then neutralized by means of an alkaline or alkaline-earth base, filtered and analysed.

The end product of approaches described in methods a) to c) is a sulphate ion that can be analysed with different techniques. The most common techniques are turbidity, ion chromatography and HPLC. Turbidity techniques are cheaper, very easy to handle not only for chemists and useful in lab and in field application.

In method d) the rinsed and dried copper is treated directly in its vial with a reducing agent like metal-boron-hydride; e.g. sodium tetraborohydrate or a metal hydride in the presence of a small quantity of water (1-5 ml). Hydrogen sulphide can be quantified with a portable gas analyser or through GC-FID, TCD, FPD or AED.

4.2.3 Determination and Quantification of Sulphur Corrosive Compounds on Paper, Cover Copper Deposition—Improvement of CCD Test The methods described in 4.2.2.2 a) can be surprisingly applied also to other parts of the equipment that are in contact with the fluid. These are particularly well suited for quantitative determination of $Cu_2S$ on insulating Kraft paper in electrical transformer and equipment. Thus it represents a very significant improvement for the assessment of corrosivity of mineral oils over the empirical qualitative tests such as the CCD test. For the quantitative determination at the end of the CCD test, the insulating paper and the copper strip are taken out of the vial, rinsed with a light hydrocarbon solvent (pentane, n-hexane, heptane, isooctane), dried and transferred in a second borosilicate glass vial in which a small amount of an alkaline hydroxide (from 0.01 to 1 g) is added. The vial is sealed and heated up to (250°-650° C. typically 500) by the help of a flame or electrical resistance. During the heating stage, pure oxygen is made to flow through the vial with the two needles inserted in the sealing cap. The oxidation is carried on for several minutes (from 5 to 60, typically 20), then the contents of the vial are allowed to cool down to ambient temperature, a few grams of de-ionised water (5-20 typically 10) are added to the vial and the solution is boiled for several minutes (5-20 typically 10) with a gentle stream of oxygen.

The sulphate solution is filtered on a nylon filter (0.45 μm) and analysed with different techniques and in particular turbidity, ion chromatography and HPLC.

The same procedure described for paper can be applied on copper strip of CCD test.

The process can be applied to quantification of inorganic deposits resulting from corrosion of other components in electrical equipments through oxidation or reduction.

4.2.4 Conversion Calculations

DBDS or other corrosive sulphur compounds react with copper, forming copper sulphide, that to be quantified, is converted in copper sulphate or hydrogen sulphide. Thus this approach permits quantitative determination of corrosive sulphur in oil.

To determine the amount of corrosive sulphur that reacts with copper, some calculations have been carried out; through the following algebraic expressions the amount of corrosive sulphur ($S_{corr}$) expressed as mg of sulphur (corrosive) per Kg of fluid is obtained.

In case copper sulphide is converted in cupric sulphate:

$$S_{corr} = [(C_{sulph} \times V_{sol}/96.06) \times 32.07]/Kg_{oil} \qquad \text{eq. 6}$$

where $C_{sulph}$ is the concentration of sulphate iones (in mg/L) in solution at the end of the test (described in 4.2.2.2)

96.06 è is the molecular weight of the sulphate $V_{sol}$ is the volume in liters of the sulphate solution $Kg_{oil}$ is the amount of oil used in the test.

In case copper sulphide is converted in hydrogen sulphide:

$$S_{corr} = [(C_{HS} \times V_{sol}/33.07) \times 32.07]/Kg_{oil} \qquad \text{eq. 7}$$

where $C_{HS}$ is the concentration of hydrogen sulphide (in mg/L) at the end of the test (described in 4.2.2.2)

33.07 is the molecular weight of the hydrogen sulphide $V_{sol}$ is the volume (in L) of the vial containing the hydrogen sulphide $Kg_{oil}$ is the amount of oil used in the test.

However, this expression does not allow one to discriminate between oil with no additives and oils containing additives. Distinction between such oils can be made with an expression given in eq. 8. This expression permits classification of oils in regards to the amount of corrosive compounds and the presence of additives (e.g. passivators). Such coefficient Xs (coefficient of corrosive sulphur) can be calculated as follows:

$$X_s = \log[(S_{corrFin} \times S_{corrXmin}/k) + 1] \qquad \text{eq. 8}$$

$S_{corrXmin}$ and $S_{corrFin}$ are the quantity of corrosive sulphur calculated according to the formula above, after the treatments described in 4.2.2. $S_{corr}X_{min}$ is the value of corrosive sulphur after a limited contact time between oil and copper (e.g. 120'), whereas $S_{corrFin}$ is the value obtained after a prolonged interaction (e.g. 720'). In case of a non-corrosive oil, the value of $H_s$ will be 0.

K is a coefficient allowing a result included between 0 and 1, for example 1886. This value is obtained by considering 500 mg/Kg of DBDS as the maximum amount of equivalent corrosive sulphur available in a fluid (as statistically happens in the greater part of practical cases of contamination). This concentration is turned into $S_{corrFin}$. If the oil is not passivated $S_{corrXmin}$ ($X_{min}$=120) and $S_{corrFin}$ coincide. So if one multiplies $S_{corrXmin}$ by $S_{corrFin}$ and divides the results by 9 the result is 1886.2391 (approximated to 1886). In case of oil containing 500 mg/Kg of DBDS Xs is 1. In fact: Xs=log(9+1). Consequently all results are comprised between 0 and 1.

Also, it could be useful to know the quantity of corrosive sulphur "masked" by the passivating additives, i.e. the component of corrosive sulphur capable of attacking the metal (copper) not evaluated through the CCD test. This can be expressed as a percentage and is:

$$H_s = [(S_{corrFin} - S_{corrXmin})/S_{corrFin}] \times 100$$

where $S_{corrXmin}$ and $S_{corrFin}$ are those defined in the preceding formula and $H_s$ is the coefficient of hidden corrosive sulfur. It is correlated to the corrosivity that is not manifested through qualitative and subjective tests such as the CCD test.

The amount of copper sulphide deposited ($S_{corr}$) on copper strip or paper wrapping it (see 4.2.3) is calculated according to:

$$S_{corr} = [(C_{sulph} \times V_{sol}/96.06) \times 32.07]/Kg_{paper}(mm_{copper}^2)$$

where $C_{sulph}$ is the sulphate ion concentration (in mg/L) in solution at the end of the test (described in 4.2.2.2)

96.06 is the molecular weight of the sulphate $V_{sol}$ is the volume (in L) of the sulphate solution $Kg_{paper}$ is the weight of paper $mm^2_{copper}$ is the surface of copper strip 4.3 Accelerated Ageing and Non-Sulphur Corrosion Test The ability of oils to withstand oxidative degradation under thermal stress is of fundamental importance, since oxidative degradation leads to several changes in the oil e.g. it increases concentrations of oxygenated polar compounds such as organic acids, increases viscosity and leads to the formation of insoluble oligomers or polymers, These chemical changes have effects on the dielectric and thermal properties. Therefore, a method that provides greater and precise information in the shortest amount of time regarding the chemical composition of the oils subject to thermo-oxidative stress is desired. The methods developed and described in this document are able of providing in short times a set of comprehensive data, with a specific extension to the corrosion phenomena not correlated to the presence of corrosive sulphur. This method presents several innovative aspects (among them the use of vials, copper powder or granules, continuous stirring and the possibility of determining the quantity of oxygen present and the gases generated) that make the procedure surprisingly fast. That in turn leads to the ability to perform a higher number of analyses in a shorter time (1-4 hours versus at least 162 hours minimum required in the case of standard EN 61125 for not inhibited oils and 500 hours for inhibited oils).

The first step is the reaction between oxygen and a weighed amount (5-50 g, typically 25 g) of liquid (e.g. insulating oil) in the presence of a weighed amount (0.5 to 10 g, typically 3 g) of powder or granular (1 μm to 5 mm, typically 40 μm) copper at temperature above 100° C. (100-200, typically 120° C.-150° C.) in a gastight borosilicate glass throwaway and pre-treated vial (volume 10 to 100 ml, typically 50) sealed by butyl/PTFE rubber septum with continuous stirring employing a teflon covered magnetic needle for several hours (from 1 to 600). To perform such a reaction, an innovative heating and stirring apparatus that can process several samples simultaneously is used (see 4.1). The vial can be either saturated with oxygen or air and then kept sealed in the "revolving table" apparatus (see 4.1) or the vials can be continuously purged with a flow of air or oxygen through needles on the septum and pipes connected to the other vials with a known volume filled with reacting gases. In case of sealed vials the evolved volatile compounds such as short chain acids and oxidized species are sampled from headspace and analysed (e.g. dissolved gas analysis—DGA, etc). In the case of purged vials the purged gases are made to pass through a suitable solvent (e.g. a basic aqueous solution NaOH 0.1M) that can entrap the most polar and acidic compounds. This aqueous solution may undergo specific analyses (basic titration, chromatographic analyses HPLC, GCMS). At the end of the oxidation reaction the oxidized fluid is decanted away from copper and kept ready for further analyses in a second vial. The typical analyses are: dissolved or suspended copper content (ICP or atomic absorption technique), formation of sludge, water content, neutralisation number, oxidised and acid components (FTIR and GCMS technique).

4.4 "Fingerprinting" of the Oil

Oil is mainly characterised by the determination of specific profiles of the ether atoms present, such as sulphur, oxygen, nitrogen that are correlated to the profile of carbon and the distillation curves.

The profiles are obtained by using high-resolution gas chromatographic separation techniques (HRGC) coupled with detectors such as AED (atomic emission detector) and MS (mass spectrometry).

The study of the profiles allows, first of all, establishing the nature of the oil (e.g. naphtenic, paraffinic, or hydro cracked) and the presence of some specific additive declared or not by the manufacturer (e.g. DBDS and DBPC).

Subsequently, a comparison between the profiles prior, during and after the corrosivity and aging tests is carried out, with the purpose of determining through matching, specific variation leading to the effect of the corrosive action and the presence and interaction of the additives present in the oil (see examples).

4.5 Functional Diagnosis

Through the interpretation of the facts (anamnesis, visual signs, analytical results, velocity, measure uncertainty) relative to the evaluation of the risks associated with corrosive sulphur and aging, it is possible to scientifically predict the effects of the action of the corrosive and oxidised compounds inside the equipment containing the oil. The determination of the kinetics of the formation of determined corrosive, oxidised species and the relevant by-products, the dissolved gases and copper, is the fundamental instrument to evaluate the quality and quantity of the effects of the mechanisms involved influencing the reliability of the components or the equipment itself. A typical example is the indirect quantification of the copper sulphide produced through the quantification of DBDS and its by-products, in particular bibenzyl (see clause 4.2).

4.6 Decontamination, Selective Depolarisation and Detoxification of Oils

This invention provides test methods, reagents and formulations for targeted treatments aimed at ensuring the best functional and/or environmental performances of the oil, through decontamination, selective depolarisation (from corrosive, polar and oxidised compounds, and by-products which have a negative impact on the thermal and dielectric properties) and the detoxification from dangerous contaminants and other additives (POPs, passivators derivative of BTA).

Since each oil is different from another one, in order to obtain the optimised formulation of the reagents described here below, it is fundamental to perform preliminary "treatment tests" of the oil, going to integrate the tests described here above (corrosivity, ageing and fingerprinting). These decontamination, depolarisation and detoxification tests are carried out on a lab scale in vial, according to the modalities described here above (see 4.1, revolving table, stirring apparatus, and reagent 5% in weight) and allow identifying and using the best formulations of reagents for the different applications. The tests are focused toward the determination of the technical and financial feasibility of the treatments, the quality control of the reagents and the traceability of the production lots.

At present, this type of treatment is carried out through the passage of oil through adsorbents, primarily Fuller's earth, with very limited success and potential cross-contaminations (e.g. DBDS and PCBs). The methods described herein are much more efficient and can be performed either in continuous mode or in batch mode, closed loop without an even partial draining of the equipment, also under load mode, by using a specific system (decontamination mobile unit—DMU), that can be used both in the field and dedicated centres. The methods provide the heating of the oil to the required temperature (up to 200° C., typically between 60 and 100° C.) in the presence of specific reagents. The apparatus can be made of several containers (e.g. columns) able to operate in series or parallel or a reactor operating under dynamic stirring and mixing conditions (under positive or negative pressure). The process can also be assisted by the irradiation of ultrasounds, microwaves and UV.

The reagent mixture can be made of different substances, adsorbents, salts and metals, depending on the type of compounds that have to be removed. The aim of the mixture is to remove the oxidized and corrosive compounds, neutralize acidity and improve physical and chemical properties of the oils. The reagent can be typically composed of one or more of the following substances, in a variable proportion based upon the treatment to be carried out:

1) An adsorbent of general formula $SiO_2$ $nH_2O$ (silica gel), where n is a variable number of water molecules. For the adsorption of polar and oxidised species (aldehydes, ketones).
2) An adsorbent of general formula $Al_2O_3$ neutral, acid or basic allumina) for the adsorption of sulphur compounds and water.
3) Activated carbon. For the adsorption of sulphur, oxidised and polar compounds. It also has the function of high surface catalytic support (up to >1000 m2/g) and facilitates the chemical decomposition reactions and being one of the best absorbents of microwaves, also for the subsequent re-functionalisation treatment of the entire saturated reagent.
4) A solid particulate with high surfaces area such as pumice, bentonite, olivine, perlite, alkaline and earth-alkaline carbonates or bicarbonates.
5) An alkaline metal hydroxide or alkaline earth hydroxide for the decomposition of sulphur and halogenated compounds.
6) An hydrogen donor like polyalkylenglycols of general formula $R(OC_xR_1R_2)_nOH$ where x is >2, n is a integer number between 2 and 500, R is Hydrogen, $C_1$-$C_{20}$ linear or branched alkylen group, $R_1$ and $R_2$, equal or different, are hydrogen, linear or branched alkylen group, if necessary substituted by $C_5$-$C_8$ cicloalkyl or aryl or random copolymer of propylene and ethylene oxides.

7) Non alkali metals like aluminium, calcium, magnesium, copper, manganese, nickel, palladium, titanium, zinc, tin and their mixture/s as catalyser for chemical reactions for the decomposition of sulphur and halogenated species.

8) Metals or alloys can be present in the reaction ambient with high surfaces or under the form of spheres (from 0.5 mm to 50 mm) able to improve catalytic effects, heat transfer, mixing capability and easier materials recovery. The metal content varies typically from 0.01 through 5% in weight with respect to the total weight of the reagent.

All the hygroscopic components must be previously dried and impregnated by additive-free oil compatible with the type of specific application. The oil has also the function of eliminating the critical factors linked to the formation of air bubbles during the treatment, minimising the subsequent need to use certified top-up oils.

It was surprisingly observed that the appropriate mixture of these compounds can remove or decompose most of the contaminants such as acidic compounds, aldehydes, ketones, sulphur corrosive compounds (like DBDS). The mixture of reagents can also purge BTA and/or its derivates, and some POPs (PCBs). It should be pointed out that BTA and its derivatives are not necessary in liquids that do not contain corrosive sulphur compounds. Furthermore, it was observed that the removal of oxidized species from PCBs (polychlorobyphenyls) contaminated oils, surprisingly affects positively the speed and rate of dehalogenating reactions performed in compliance with Sea Marconi's patent no EP 0675748 ("Process for the chemical decomposition of halogenated organic compounds").

For the subsequent re-functionalisation treatment of the reagent it is fundamental the use of a thermal and pyrolysis desorption system with or without vacuum. The adsorbed species can be desorbed from the reagent mixture by means of solvents or heat and gas flow or heat and vacuum and microwaves. Water or ethanol can be used to solubilise polar species. Once the components have been recovered, some solid supports can be reused for preparation of fresh reagent.

EXAMPLES

Figure 2:
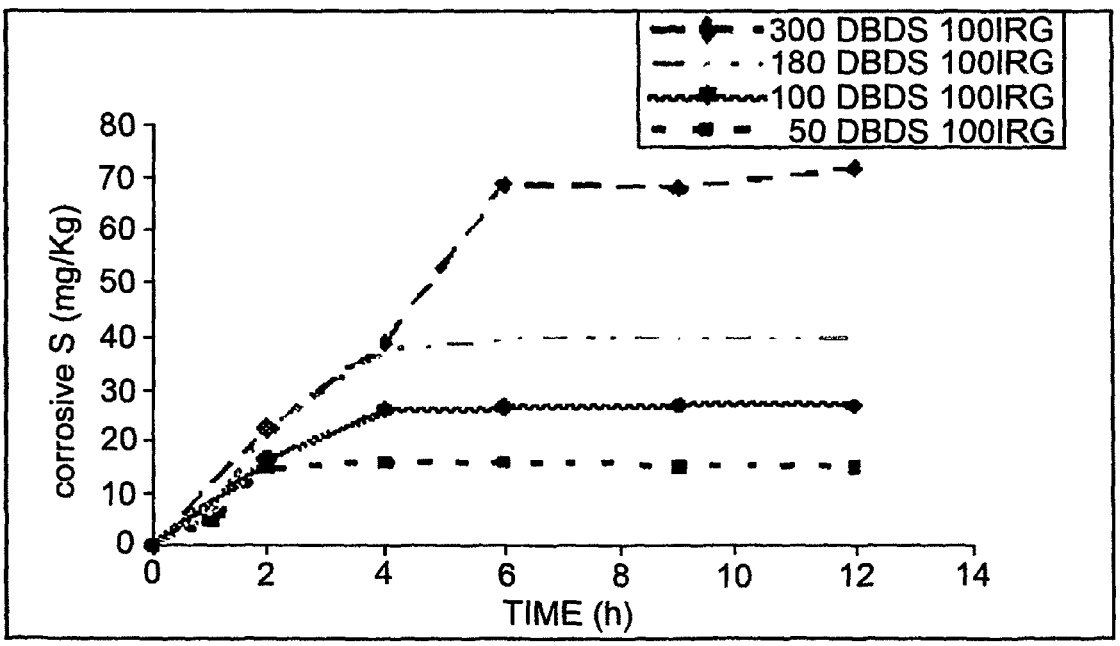
Figure 3:
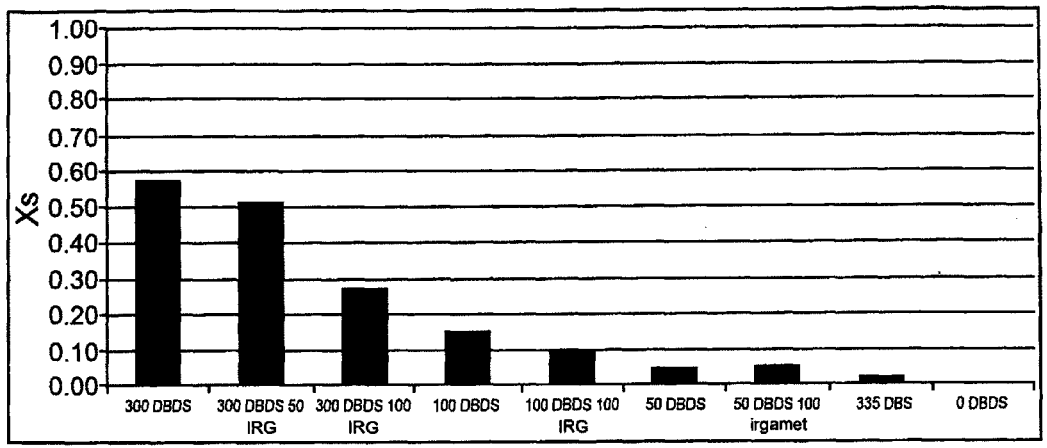
Figure 4:
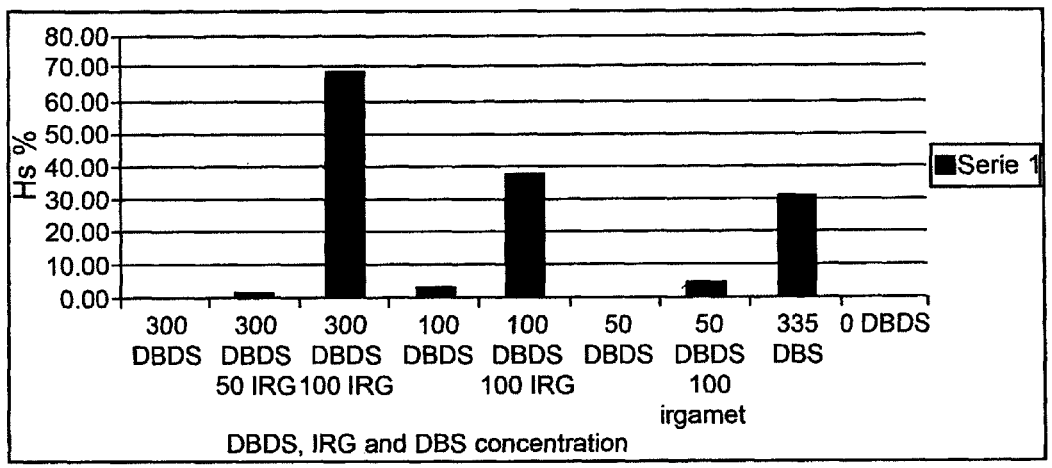
Figure 5:
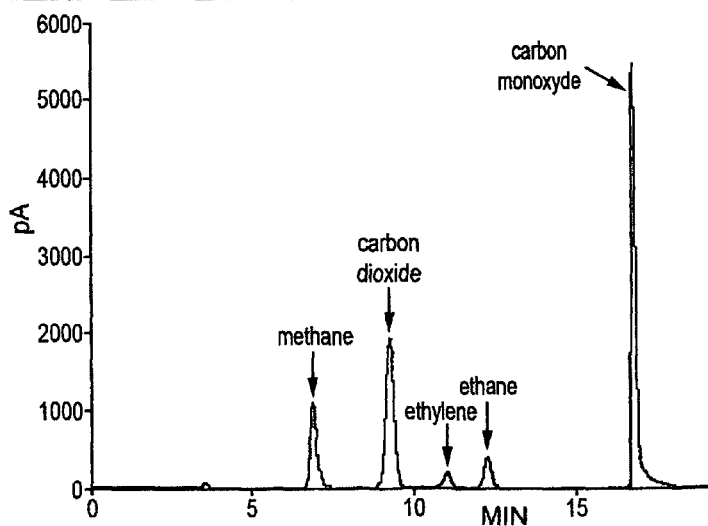
Figure 6:
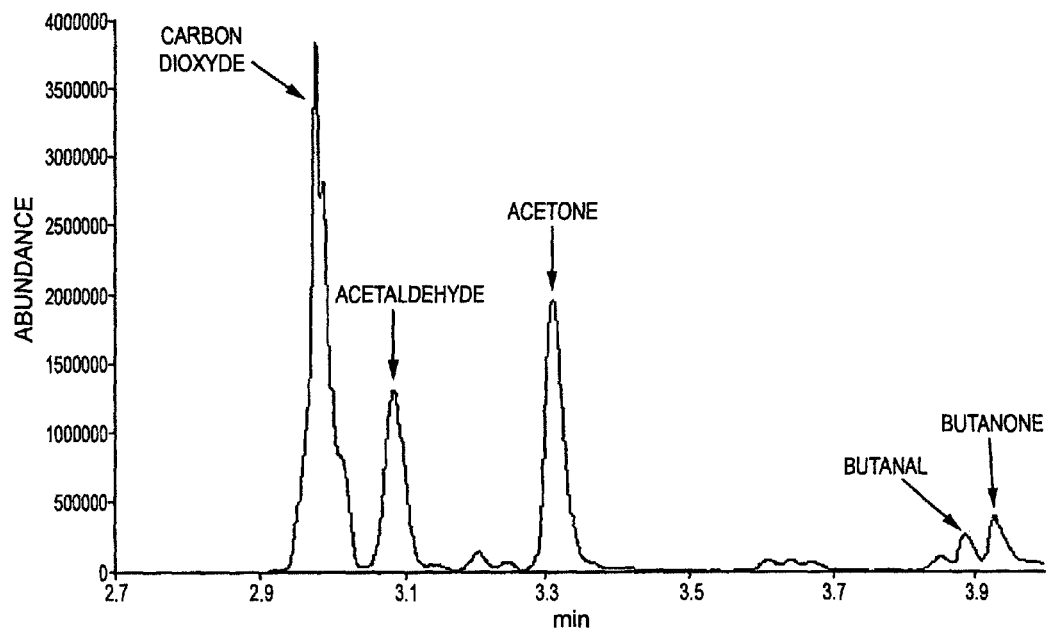
Figure 7:
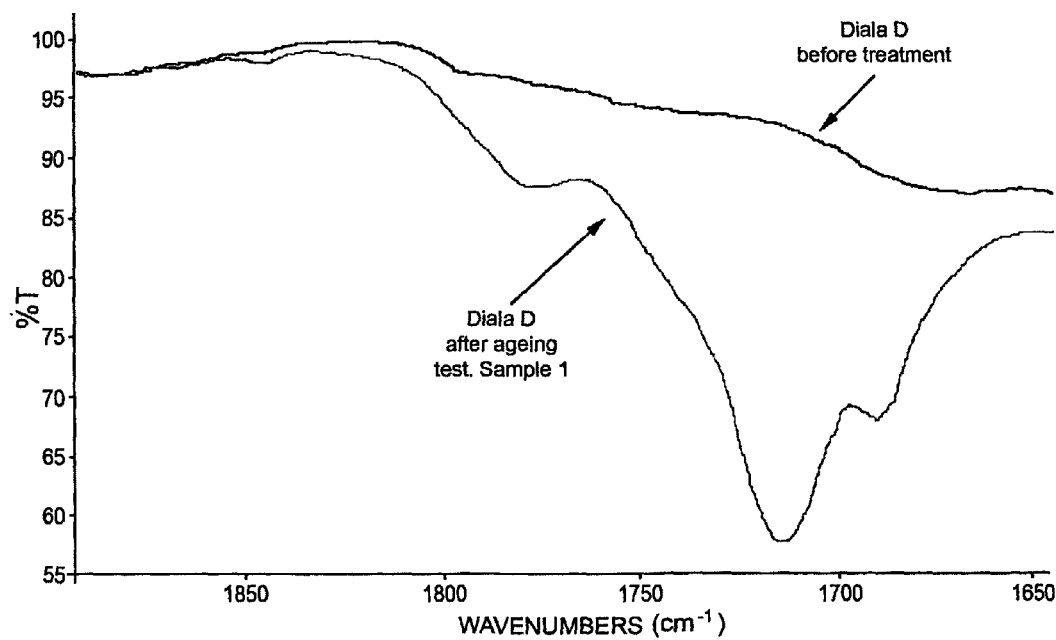
Figure 8:
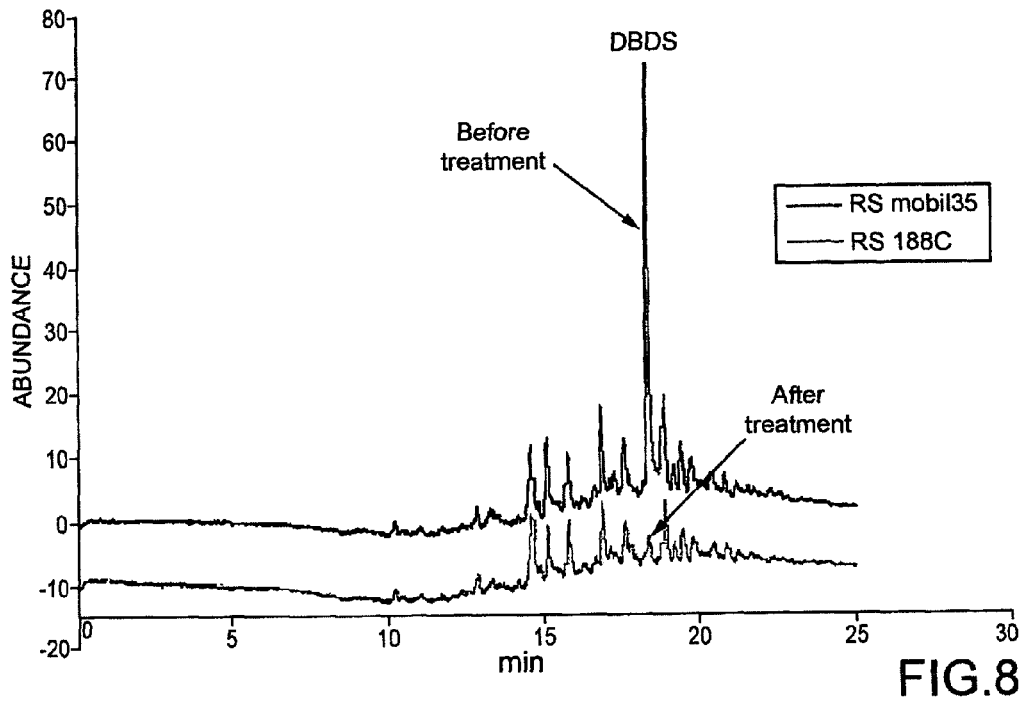
Figure 9:
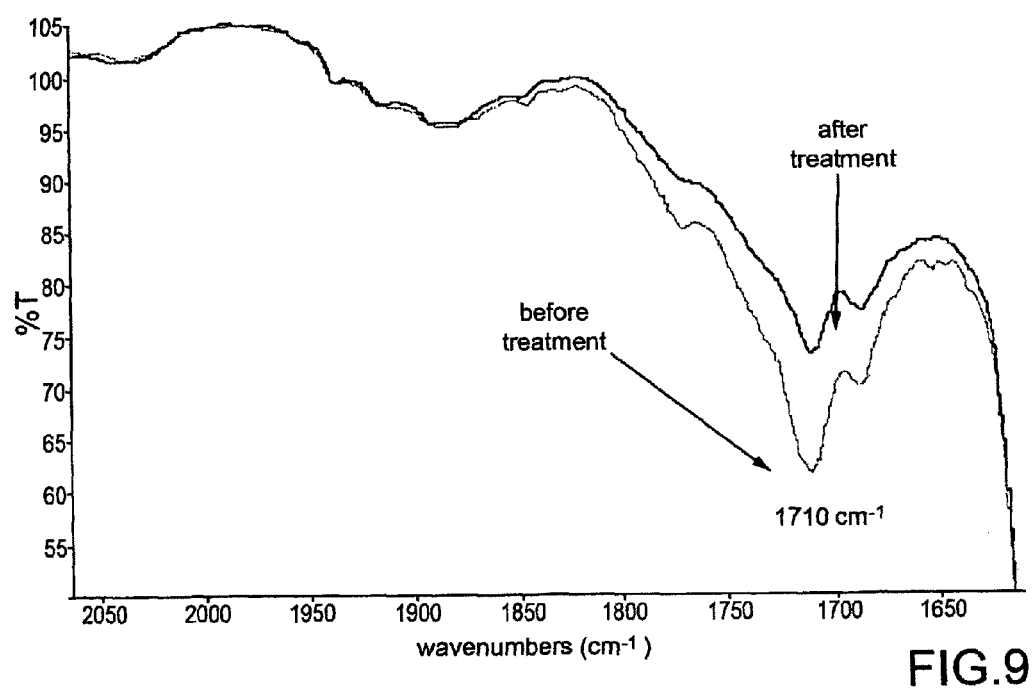
Figure 10:
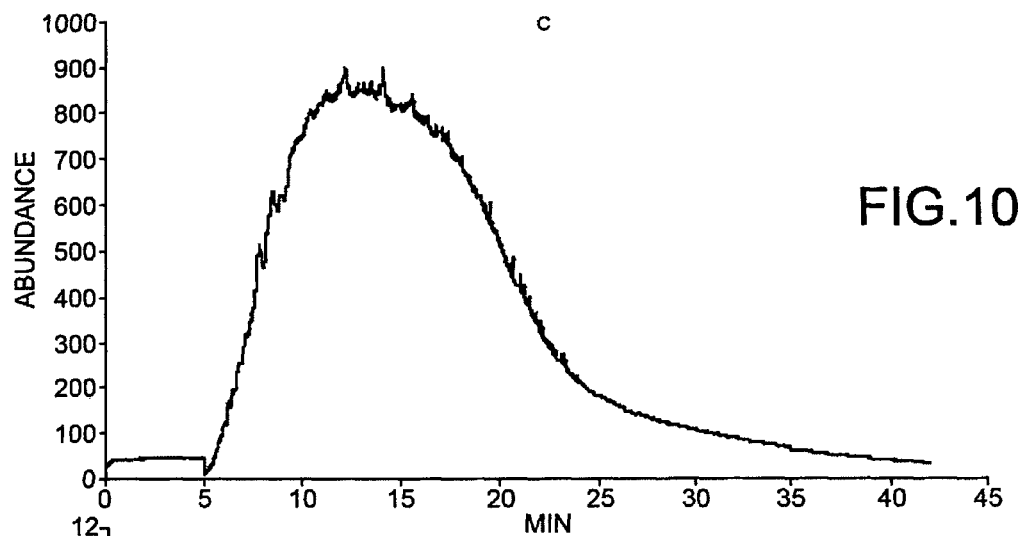
Figure 11:
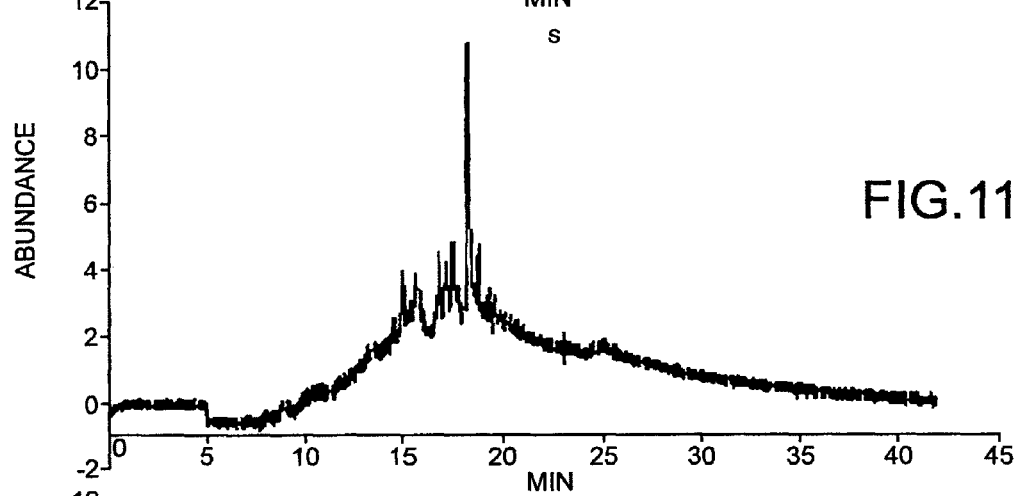
Figure 12:
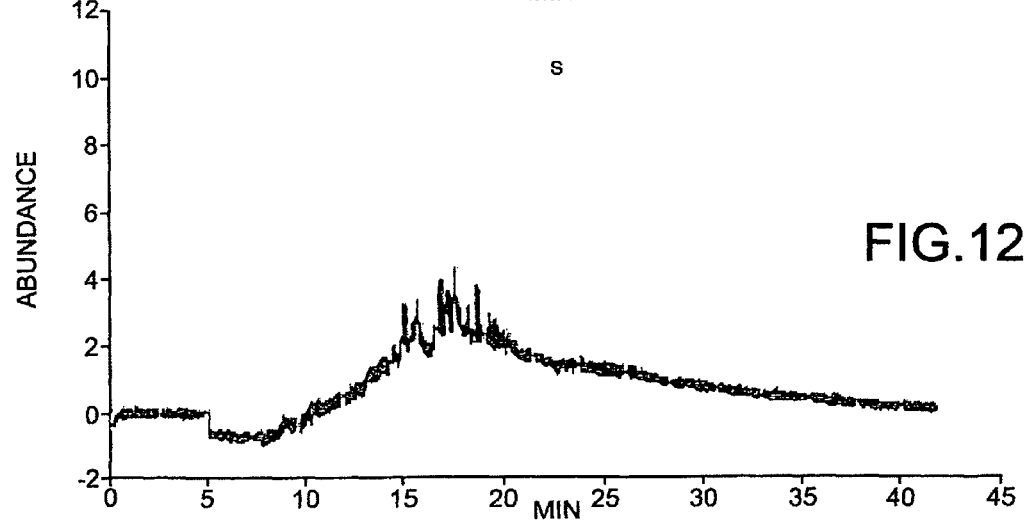

The examples here below are described with reference to the enclosed drawings, in which:

FIG. 1 is a graph reporting as a function of time, the amount of corrosive sulphur resulting from the reaction of the DBDS with copper, FIG. 2 is a graph reporting as a function of time the amount of corrosive sulphur resulting from the reaction of the DBDS with copper in oil containing a passivator, FIG. 3 is a diagram reporting the coefficients of corrosive sulphur (Xs) for various samples, FIG. 4 is a diagram reporting the coefficients of hidden corrosivity (Hs) for various samples, FIG. 5 illustrates a chromatogram (GC-FID) of the volatile compounds sampled in the headspace, FIG. 6 illustrates a chromatogram (GC-MS) of the volatile compounds sampled in the headspace, FIG. 7 illustrates a FTIR spectrum before and after the accelerated ageing test, FIG. 8 illustrates a chromatogram GC-AED before and after a depolarisation treatment, FIG. 9 illustrates the FTIR spectrum of the oil before and after the treatment and emphasises the reduction of the band relative to the carbonylic groups, FIG. 10 illustrates the profile of carbon (GC-AED analysis) of oil Shell Diala D, FIG. 11 illustrates the profile of sulphur (GC-AED analysis) of oil Shell Diala D, e FIG. 12 illustrates the profile of sulphur (GC-AED analysis) of oil Shell Diala D after reaction with copper powder at 150° C. for 4 hours.

Example 1

"Corrosive Sulphur" Tests on Non-Passivated Oil

The tests have been carried out complying with what described in clauses 4.1.1.1 and 4.1.1.2a) on oil Shell Diala D contaminated by a different amount of DBDS (50, 100, 180 e 300 mg/kg); to create blanks sulphur-free oil has been used. 3 grams of copper powder (particle size 40 μm) have been used.

After the preparation phase, the samples were placed in a heating stirring system (see clause 4.1) and heated at 150° C. for different times variable from 1 to 12 hours (1, 2, 4, 6, 9, 12 hours). At the end of the first phase of reaction times, the vials were allowed to cool down to ambient temperature before the seal was removed; the oil aliquots were separated from the copper and placed into other containers for additional analyses. Each copper aliquots were rinsed 3 times with 15 ml of isooctane, once with 15 ml of pentane and then dried under a gentle stream of air.

Then 0.15 g of sodium hydroxide has been added to each sample. The vials were sealed and heated to a temperature between 250° and 500° C. using a Bunsen burner. During this passage, oxygen was purged through two needles (one inlet and one outlet). The oxidation was continued for 20 minutes, then the samples were allowed to cool down to ambient temperature, 10 ml of de-ionised water were added and the suspension was boiled for 10 minutes under a mild flow of oxygen. The resulting suspension, containing copper sulphide, was then filtered, diluted up to 20 ml with de-ionised water and analysed by turbidity adding 0.15 ml of concentrated hydrochloric acid and 90 mg of barium chloride. The result obtained for the blank was 6 mg/kg of sulphates, value that has been subtracted for the results of other experiments, indicated in FIG. 1, where the concentrations of corrosive sulphur deriving from the presence of DBDS in mineral oil are listed. The results demonstrate how after one-hour reaction more than 90% of the DBDS added to the oil is converted in copper sulphide, quantitatively determined as sulphate.

Example 2

Corrosivity Tests on Passivated Oil

The tests described in example 1 have been repeated on oil passivated with Ciba Irgamet® 39 in concentration 50 or 100 mg/kg. The results obtained by turbidity are listed in FIG. 2, showing the concentrations of corrosive sulphur deriving from the presence of DBDS in the mineral oil containing the passivators. The results demonstrate that, also when Ciba Irgamet® 39 is present, 90% of the DBDS added to the oil gets converted into copper sulphide within a 4 hour period, clearly illustrating that the protective action of the passivators is only temporary, also highlighting the fact that the method described in this document can be used to discriminate between a passivated and non-passivated oil.

The corrosive sulphur coefficient ($X_s$) and the hidden corrosivity co-efficient ($H_s$) can be calculated (eq. 7) and used for classification of oils. Such application is demonstrated in Table 1 and in FIGS. 3 and 4. Corrosivity is higher (higher value of $X_s$) when the DBDS concentration and/or the ratio between DBDS and Ciba Irgamet® 39 concentration is highest.

Example 3

Determination of Copper Sulphide on Copper Strip and on Insulating Paper

CCD tests were performed with an oil sample taken from an electrical transformer contaminated by DBDS.

At the end of CCD test the copper strips, wrapped in paper, were taken out of the vials, rinsed with isooctane, cyclohexane and allowed to dry in air. Once dried, the copper strips were cut in 2 parts and transferred into 20 ml vials; two grams of copper powder were added to each sample, then 0.150 g of sodium hydroxide were added to each sample. The vials were sealed and heated to a temperature between 250° and 500° C. using a Bunsen burner. During this passage, oxygen was purged through two needles (one inlet and one outlet). The oxidation was continued for 20 minutes, then the samples were allowed to cool down to ambient temperature, 10 g of de-ionised water were added and the suspension was boiled for 10 minutes under a mild flow of oxygen. The resulting suspension, containing copper sulphate, was then filtered, diluted up to 20 ml with de-ionised water and analysed by turbidity adding 0.15 ml of concentrated hydrochloric acid and 90 mg of barium chloride.

The paper strips deriving from the CCD test were transferred into 20 ml vials and 0.200 g of sodium hydroxide added to each one of them. The vials were sealed and heated to a temperature between 250° and 500° C. using a Bunsen burner. During this passage, oxygen was purged through two needles (one inlet and one outlet). The oxidation was continued for 20 minutes, then the samples were allowed to cool down to ambient temperature, 10 g of de-ionised water were added and the suspension was boiled for 10 minutes under a mild flow of oxygen. The resulting suspension, containing copper sulphate, was then filtered, diluted up to 20 ml with de-ionised water and analysed by turbidity adding 0.15 ml of concentrated hydrochloric acid and 90 mg of barium chloride. The results are listed in Table II.

Example 4

Comparison with CCD Test Results, Solving Cases of Difficult Classification ("False Negative"—Non Potentially Corrosive; "False Positive"—Potentially Corrosive)

It has been observed that CCD test can provide "false positive" or "false negative" results with certain oil samples. The presence of some passivators such as Ciba Irgamet® 39 or other additives can affect the reaction between copper and corrosive compounds, and lead to misleading or incorrect results.

Therefore, the CCD test was performed both on used and new oils; the same oils were also tested according to the method described in this document. The results obtained are listed in Table III.

In case A it was evident how Ciba Irgamet® 39 is able to mask the presence of DBDS during the CCD test and how, in any case, its action is temporary only. Also, in some cases the CCD test leads to "Non Potentially Corrosive" results also for oils containing corrosive sulphur compounds ("False Negative"). In case B, the CCD test had an uncertain and dubious. On the contrary, methods 4.2.2.2 and 4.2.3 are not influenced by the presence of Ciba Irgamet® 39 and provide quantitative results solving all possible doubts about the corrosivity of the oil.

Example 5

Copper Sulphide Oxidation with $NH_3/H_2O_2$ 1 gram of copper granules (dimension of particles 40 μm) or a copper strip (30×8 mm) were put with a magnetic needle into a series of 20 ml borosilicate glass vials; then the vials were purged with Argon in an appropriate instrument ("revolving table" paragraph 4.1), sealed by appropriate butyl/PTFE rubber crimp caps and filled with 15 grams of Shell Diala D oil each. Each sample was prepared using Shell Diala D oil contaminated by a different amount of DBDS ranging between 50 to 500 mg/Kg; to create the blank, sulphur-free oil was used.

After the preparation phase, the samples were placed inside a heating and stirring system (see paragraph 4.1) and heated at a temperature between 80 and 150° C. for times ranging from 0.5 and 144 hours. At the end of the reaction times, the vials were allowed to cool-off, then open; the oil aliquots were separated from the copper and placed into other containers for additional analyses. The copper aliquots were each rinsed 3 times with 15 ml of hexane. The hexane rinsed copper (strips or granules) was allowed to dry in air at ambient temperature and then transferred to clean long neck digestion flasks, 10 ml of 35% $H_2O_2$ was added to the flasks; the contents of flasks were allowed to equilibrate at ambient temperatures for one hour. After the one hour, 15 drops of 30% $NH_4OH$ and the contents of the flask were gently shaken for 20 minutes; because the interaction between $Cu_2S$ coated strips and reagents is exothermic and quite vigorous, it is necessary to take care during operation.

At the end of the pre-established time, 4 ml $NH_4OH$ at 30% was added to each sample heating and gently swirled until the blue gels had completely dissolved, obtaining a clear solution; this solution was carefully decanted through filter paper in a graduated flask to separate the black residue. Then, 10 ml of 35% $H_2O_2$ was added to the black residue in the flask and the contents were allowed to stand for 30 minutes. Approximately 20 drops of 30% $NH_4OH$ were added to the flasks and the flasks were carefully swirled until reaction ceased. The samples were heated on hot pads and swirled until the blue gel had disappeared and clear solutions were obtained. Solutions from the second digestions were filtered and transferred to the volumetric flasks containing solutions from the first digestion bringing the volume in the flasks to the mark with "de-ionised" water. A known amount of chloride was then added as internal standard and the solution was analysed by ion chromatography, calculating the concentration of iones sulphate. Results of the experiments are shown in Table IV. The results show that the DBDS reacts quantitatively with copper forming $SO_4^{2-}$ and can be afterward determined as iones $SO_4^{2-}$.

Example 6

Accelerated Ageing on Insulating Oil and Non-Sulphur Corrosion Test

Two different kinds of tests were performed, one with no gas flow and the other with a continuous oxygen flow.
Accelerated Ageing Test without Oxygen Flow
Three grams of copper powder (particle dimension 40 µm) and a magnetic bar were placed in a series of 50 ml borosilicate glass vials, then the vials were saturated inside an appropriate instrument ("revolving table", clause 4.1) sealed by appropriate butyl/PTFE rubber crimp caps and filled with 25 grams of Shell Diala D oil each. After the preparation phase, the samples were located in a heating and stirring system (see paragraph 4.1) and heated at 120 or 150° C. for 4 or 8 hours. After the end of the reaction period, oil was subjected to set of analyses, among them:
1) TAN determination in accordance with IEC 62021-1
2) Water content determination in accordance with IEC EN 60814
3) Determination of Sludge formation in accordance with EN61125
4) Determination of the total and dissolved Copper in oil in accordance with ASTM D 7151.
The results obtained are shown in Table V and FIGS. 5, 6 and 7.
Ageing Test with Oxygen Flow
Three grams of copper powder (particle dimension 40 µm) and a magnetic bar were placed in a series of 50 ml borosilicate glass vials (vial 1); the vials were filled with 25 grams of Shell Diala D oil each. Oxygen was bubbled through the oil with a 2-needle set-up; the needles were inserted through the sealing septum of the vial. The outlet gas flow was passed through a second 50 ml borosilicate glass vial (vial 2) filled with water. Oil in vial 1 was simultaneously heated to 150° C. with continuous stirring. Heating and oxygen flow were carried out up to 4 hours. At the end of the 4 hours period the oil in vial 1 was analysed for colour and TAN and water content of vial 2 for acidity. Results of the analyses are shown in Table VI.

Example 7

Ageing Tests on Natural Ester Oils

Two different commercially available natural ester-insulating oils were used. 1.0 gram of 40 mesh copper granules and a magnetic stirring bar were poured into a series of 20 ml borosilicate glass vials, filled with 15 grams of oil each. Vials were then sealed by PTFE and butyl rubber caps, then Oxygen at 16 ml min was made flow through the vials through two needle inserted in the sealing septum of the vial. Then the samples were placed inside a heating and stirring system (described in paragraph 4.1), at a temperature of 125° C. for 4 hours. After heating cycle, oils were analysed for TAN and Kinematic Viscosity in accordance with standard test methods ASTM D 974-02 and D445-06 respectively. Results of the tests are shown in Table VII.

Example 8

Decontamination, Depolarisation and Detoxification of Mineral Insulating Oil Integrated Treatment Test 50 g of Shell Diala D oil contaminated by DBDS, Ciba Irgamet® 39 and PCBs (Aroclor 1260 mixture) were placed into a 100 ml vial containing a PTFE coated magnetic bar. After bringing the oil at a temperature of 80° C. using the heating and stirring system described in paragraph 4.1, 5.0 g mixture of potassium hydroxide (25%), polyethileneglycol 6000 (25%) and activated carbon (50%) was added to the system. Iron powder in the amount of 0.5% in weight with respect of the sum of the reagents was added to the system. The reaction system was allowed to react at 80° C. with constant stirring for 15 hours. At the end of the treatment period an aliquot of oil was removed and analysed with a GC-AED: DBDS concentration dropped from 163 mg/Kg lower than 10 mg/Kg (FIGS. 8 and 9, Table VIII); the concentration of Ciba Irgamet 39 dropped from 32 mg/Kg to less than 3 mg/kg (HPLC determination). At the end of the treatment, the oil was subject to a dehalogenation test from PCBs for 4 hours in a flask with 5% reagent, then analysed in accordance with standard IEC 61619.

Example 9

Fingerprinting

In this example the results of the GC-AED analyses of the oils deriving from the treatments described in example 1 are shown. The profiles of the carbon and sulphur emissions shown in FIGS. 10, 11 and 12 are typical of the oil being examined. After the reaction with copper, the profile of carbon remains unchanged but the one of sulphur differs, since the peak assigned to DBDS totally disappears (retention time about 19 min) and that demonstrates the complete conversion of DBDS into copper sulphide.

TABLE I

Quantification of corrosive sulphur after 2 and 12 hours reaction (according to 4.3) on DBDS and DBS contaminated oils and hidden sulphur corrosivity coefficients.

|  | 300 DBDS | 300 DBDS 50 IRG | 300 DBDS 100 IRG | 100 DBDS | 100 DBDS 100 IRG | 50 DBDS | 50 DBDS 100 Irgamet | 335 DBS | 0 DBDS |
|---|---|---|---|---|---|---|---|---|---|
| Scrr2h | 72 | 64 | 22.5 | 26.5 | 16.7 | 14.5 | 14.5 | 6.4 | 0 |
| ScorrFin | 72 | 65 | 72 | 27.5 | 26.8 | 14.5 | 15.3 | 9.3 | 0 |
| Xs | 0.57 | 0.51 | 0.27 | 0.14 | 0.09 | 0.05 | 0.05 | 0.01 | 0.00 |
| Hs | 0.00 | 1.54 | 68.75 | 3.64 | 37.69 | 0.00 | 5.23 | 31.18 | 0.00 |

TABLE II

Quantification of $Cu_2S$ on Copper Strip and Insulating Paper

| Oil | DBDS initial conc. (mg/Kg) | DBDS final conc. (mg/Kg) | CCD test result | DBDS equivalent on copper strip (mg/kg) | DBDS equivalent on paper (mg/kg) | Amount of DBDS equivalents recovered |
|---|---|---|---|---|---|---|
| Mobilect 35 | 179 | 123 | Potentially corrosive | 31 | 13 | ~80% |

TABLE III

"False Positive" and "False Negative" results

| | Oil | Initial DBDS mg/Kg | Initial Ciba Irgamet 39 mg/Kg | DBDS final mg/Kg | Ciba Irgamet 39 final mg/Kg | CCD Test Results | Corrosive S from corrosivity test on copper powder (mg/Kg) | Corrosive S from corrosivity test on copper strip and insulating paper from CCD test (mg/kg) |
|---|---|---|---|---|---|---|---|---|
| A | Mobilect 35 - unused | 179.0 | 100.0 | 146.0 | <10 | Copper: clear Paper: no deposit. "Non Potentially Corrosive" | 45 corresponds to 174 mg/Kg DBDS 97.2% agreement | <2 mg/Kg |
| B | Aged | <10 | <10 | <10 | <10 | Copper: from clear to dark brown Paper: dark, no deposit Border line: "Non Potentially Corrosive" or "Potentially Corrosive" | 12 corrosive S corresponds to 46 mg/Kg DBDS | 5 mg/Kg on Copper 2 mg/Kg on Paper |

TABLE IV

Quantification of $Cu_2S$ formed on Copper Strips.

| DBDS Conc. (mg/Kg) | DBDS (mg) | DBDS Consumed (mg) | Moles DBDS Consumed | Moles $SO_4^{2-}$ Expected | $SO_4^{2-}$ Predicted Conc. mg/Kg | $SO_4^{2-}$ Detected Conc. mg/Kg | Percent Conversion |
|---|---|---|---|---|---|---|---|
| 300 | 4.5 | 3.04 | $1.24 \times 10^{-5}$ | $2.48 \times 10^{-5}$ | 23.8 | 22.1 | 92.8 |
| 300 | 4.5 | 3.04 | $1.24 \times 10^{-5}$ | $2.48 \times 10^{-5}$ | 23.8 | 22.8 | 95.8 |
| 300 | 4.5 | 3.04 | $1.24 \times 10^{-5}$ | $2.48 \times 10^{-5}$ | 23.8 | 22.6 | 94.9 |
| 150 | 2.25 | 2.2 | $8.94 \times 10^{-6}$ | $1.78 \times 10^{-5}$ | 17.1 | 16.6 | 97.1 |
| 150 | 2.25 | 2.1 | $8.53 \times 10^{-6}$ | $1.71 \times 10^{-5}$ | 16.4 | 15.9 | 96.9 |
| 150 | 2.25 | 2.2 | $8.94 \times 10^{-6}$ | $1.78 \times 10^{-5}$ | 17.1 | 16.5 | 96.4 |

TABLE V

Ageing end points obtained after aging test

| Sample | Colour | Water [mg/kg] | TAN | Cu [mg/kg] | Sludge % m/m |
|---|---|---|---|---|---|
| Shell oil specifications according to EN61125 | — | — | 0.23 | — | 0.10 |
| 4 h 150° C. | 2 | 140 | 0.079 | <0.1 | — |
| 4 h 120° C. 3 g Cu | 3 | 119 | 0.196 | 2.94 | 0.11 |
| 4 h 150° C. 3 g Cu | 4.5 | 164 | 0.229 | 3.44 | 0.13 |
| 8 h 150° C. | 3.5 | 143 | 0.142 | — | — |
| 8 h 150° C. 3 g Cu | 6 | 221 | 0.259 | — | — |

TABLE VI

Oxidation stability end points obtained after ageing test (oxygen flow)

| Samples | Colour | TAN | Water acidity (vial 2) |
|---|---|---|---|
| 4 h 150° C. without Cu | 3.5 | 0.07 | — |
| 4 h 150° C. with 3 g Cu | 6 | 1.718 | 0.56 mg KOH/g olio |

TABLE VII

End points obtained after dynamic ageing test with natural ester insulating oils.

| Samples | Kinematic viscosity (mm²/sec) | TAN |
|---|---|---|
| Original oil 1 | 43.8 | 0.1 |
| Oxidized oil | 42.1 | 0.3 |
| Oxidized oil | 42.0 | 0.3 |
| Original oil 2 | 38.7 | 0.1 |
| Oxidized oil 1 | 40.3 | 0.6 |
| Oxidized oil 2 | 39.9 | 0.6 |

TABLE VIII

Parameters of the oil before and after depolarisation treatment.

| Parameter | Before treatment | After treatment |
|---|---|---|
| DBDS | 163 mg/kg | <10 |
| PCBs | 108 mg/kg | <2 |
| Irgamet ® 39 | 32 mg/kg | <3 |
| Neutralisation number (TAN) | 0.235 mg KOH/g | <0.01 |
| Dissipation factor | 0.042 | 0.017 |
| Water | 13 mg/kg | 6 mg/kg |
| Colour | 2.5 | 0.5 |
| IFT | 18 mN/m | 35 mN/m |

The invention claimed is:

1. A method for determining of aging and/or corrosivity of a technical fluid including at least one from among mineral insulating oils, natural and/or synthetic esters, lubricants, hydraulic fluids, oil, and diathermic fluids, used in equipment including electrical transformers, reactors, insulators, switches and turbines, for generation, transmission, distribution, and use of power, said method being based upon one or more of the following tests:

I—an accelerated corrosivity test of the technical fluid, at a first predetermined temperature for a first predetermined time, in the presence of copper, with a dedicated heating and stifling apparatus; and II—an accelerated aging test of the technical fluid, at a second predetermined temperature for a second predetermined time, in the presence of copper with a dedicated heating and stifling apparatus, wherein each of the accelerated corrosivity test and the accelerated aging test comprise the steps of:

preparing vials with a volume from 10 to 100 ml in a dedicated revolving table containing from 1 to 100 seats for the vials;

introducing the technical fluid into the vials; and sealing the vials with caps to maintain a controlled atmosphere, and wherein the accelerated corrosivity test further comprises obtaining diagnoses and quantitative evaluations of a level of corrosivity of metal components of the equipment in contact with the technical fluid through the monitoring of the concentration of corrosive organo sulphur compounds including DBDS and the relevant degradation by-products including at least one from among bibenzyl, stylbene, toluene, dibenzyl sulphide, as well as their formation velocity, the quantification being obtained through gas chromatographic separation techniques and detection techniques including at least one from among ECD, AED, and MS.

2. The method according to claim 1, wherein, the vials comprise borosilicate glass, the caps comprise butyl rubber/PTFE, and said controlled atmosphere comprises argon, nitrogen, oxygen, and air.

3. The method according to claim 2, further comprising using a timer equipped apparatus capable of heating and stirring, by magnetic agitation from 0 to 1500 rpm, and maintaining a temperature of the technical fluid in the vials between 0° C. and 350° C., the caps of the vials being located outside a housing of the vials to reduce the thermal stress in a zone where the vials are sealed with the caps, wherein the vials contain a magnetic stirring bar.

4. The method according to claim 1, wherein the accelerated corrosivity test further comprises:

treating copper in a strip or powder form at the first predetermined temperature in a basic ambient by alkaline hydroxide saturated by oxygen;

subjecting the copper to a rinsing phase and putting the copper into a vial among the vials together with 50 to 300 mg of an alkaline hydroxide powder;

sealing the vial;

purging oxygen continuously through two openings on a sealing septum of the vial and heating at the first predetermined temperature for the first predetermined time;

cooling;

adding between 5 to 15 ml of distilled or deionised water;

boiling for 5 to 20 minutes under an oxygen flow; and filtering and analysing a resulting solution for copper salts.

5. The method according claim 4, wherein the resulting solution is analysed for copper salts with techniques including at least one of turbidity, ionic chromatography, high performance chromatography (HPLC) and capillary and packed gas chromatography coupled with TCD, FID, FPD or AED detectors.

6. The method according to claim 1, wherein the accelerated corrosivity test further comprises:

an extraction and reaction process comprising:

prior to separating the technical fluid from copper in a powder or strip form, treating the copper with a mixture of hydrogen peroxide and ammonia, wherein a vial among the vials containing the copper purified from the treating is added with 1-10 ml of a solution of 25-30% ammonia solution and left under magnetic for 60 to 240 minutes, and wherein a resulting ammoniacal solution of copper sulphide is transferred into a second vial among the vials, reduced to a smaller volume of 1-5 ml, by means of a heating, and 5-20 ml of 25-30% hydrogen peroxide is added, wherein the extraction and reaction process being repeated from 1 to 4 times and, once oxidation is completed, residual hydrogen peroxide is evacuated by heating and a resulting solution is filtered and analysed for copper salts.

7. The method according to claim 1, wherein the accelerated corrosivity test further comprises a cleaning phase of copper in a powder or strip form involving a treatment the copper with 5-10 ml of aqua regia, wherein a resulting solution is neutralised by means of an alkaline or alkaline-earthy base, and filtered and analysed for copper salts.

8. The method according to claim 1, wherein the accelerated corrosivity test further comprises a reduction of copper with a metallic hydride, wherein the copper is treated with a reducing agent including one of 0.01-1 g of sodium boron hydride and lithium aluminium hydride, in the presence of 1-5 ml of water, and wherein a released gas is analysed for copper salts.

9. The method according to claim 1, wherein the preparing the vials is done in an oxidising atmosphere on 5-30 g of the technical fluid in presence of a magnetic bar and powdered copper having a granulometry between 0.01 to 2 mm and at the first predetermined temperature under stirring conditions for the first predetermined time, wherein the caps comprises one from among butyl rubber and PTFE septum, wherein the first predetermined temperature is between 100° C. and 200° C. and the first predetermined time is between 1 and 100 hours, and wherein said vials, reagents, and preparations are provided in single use and pre-dosed kits.

10. The method according to claim 9, wherein at the end of the preparing the vials, an analysis and quantification of at least one parameter chosen from among:

gases evolved in a head space by gas chromatographic techniques coupled with FID, TCD, AED, Ms, detectors, total acidity in the technical fluid, acidity of a bubbling solution, metal content in the technical fluid, an infrared spectrum and determination of the carbonyl band, an AED gas chromatographic profile of the hetero atoms (S, N, O) and of carbon, water content in the technical fluid, and a dissipation factor of the technical fluid.

* * * * *